US007637908B1

(12) United States Patent
Gonzalez-Hernandez

(10) Patent No.: US 7,637,908 B1
(45) Date of Patent: Dec. 29, 2009

(54) SYSTEM AND METHOD FOR INTRAMEDULLARY SUBCHONDRAL SUPPORT FIXATION OF RADIAL HEAD FRACTURES

(76) Inventor: Eduardo Gonzalez-Hernandez, 3773 Matheson Ave., Coconut Grove, FL (US) 33133

( * ) Notice: Subject to any disclaimer, the term of this patent is extended or adjusted under 35 U.S.C. 154(b) by 377 days.

(21) Appl. No.: 11/449,064

(22) Filed: Jun. 8, 2006

(51) Int. Cl.
  *A61B 17/58* (2006.01)
(52) U.S. Cl. ..................... 606/62; 623/20.11
(58) Field of Classification Search .......... 606/53, 606/60, 62, 86 R, 59, 63, 64, 280, 281, 286; 623/20.11, 59, 60
See application file for complete search history.

(56) References Cited

U.S. PATENT DOCUMENTS

2006/0015101 A1* 1/2006 Warburton et al. ............ 606/62
2007/0123878 A1* 5/2007 Shaver et al. ................ 606/64
2008/0091203 A1* 4/2008 Warburton et al. ............ 606/62

OTHER PUBLICATIONS

AR Guha, ER Jago. A new technique of fixation of radial head fractures using a modified tubular plate. Journal of Postgraduate Medicine. Year : 2004 | vol. 50 | Issue : 2 | p. 113-114. Accessed Aug. 6, 2008 at: http://www.jpgmonline.com/article.asp?issn=0022-3859;year=2004;volume=50;issue=2;spage=113;epage=114;aulast=Guha.*

* cited by examiner

*Primary Examiner*—Thomas C Barrett
*Assistant Examiner*—David W Bates
(74) *Attorney, Agent, or Firm*—Feldman Gale PA; Michael C. Cesarano; Richard Guerra

(57) ABSTRACT

A system for intramedullary subchondral support fixation of radial head fractures is disclosed. An illustrative embodiment of the system includes an insertion plate having a head segment, a neck segment extending from the head segment, at least one shaft segment extending from the neck segment and at least one tail segment extending from the at least one shaft segment. A plurality of fastener openings may be provided in the insertion plate and a plurality of fasteners may extend through at least two of the plurality of fastener openings, respectively. A method for intramedullary subchondral support fixation of radial head fractures is also disclosed.

3 Claims, 5 Drawing Sheets

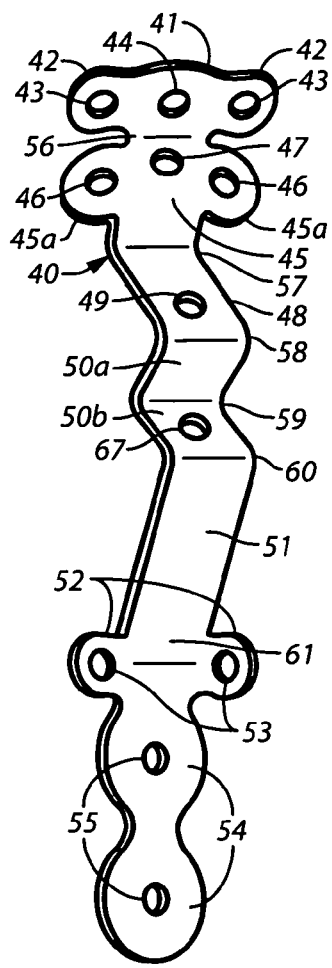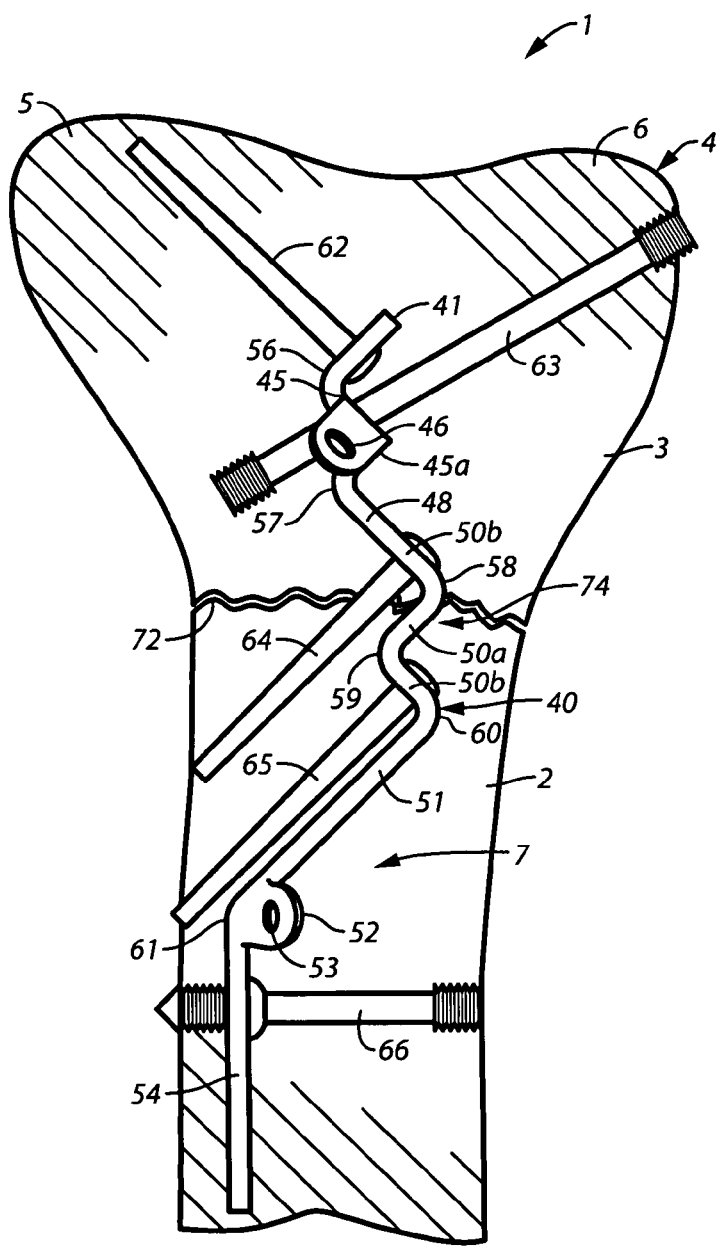
FIG. 5  FIG. 6

SYSTEM AND METHOD FOR INTRAMEDULLARY SUBCHONDRAL SUPPORT FIXATION OF RADIAL HEAD FRACTURES

CROSS-REFERENCES TO RELATED APPLICATIONS

This application claims the benefit of U.S. Provisional Patent Application Ser. No. 60/657,973, filed on Mar. 2, 2005; co-pending U.S. Non-Provisional patent application Ser. No. 11/079,350, filed on Mar. 14, 2005, which claims the benefit of U.S. Provisional Patent Application Ser. No. 60/552,632, filed on Mar. 12, 2004; and co-pending Non-Provisional patent application Ser. No. 11/050,304, filed on Feb. 3, 2005 claiming the benefit of co-pending Non-provisional patent application Ser. No. 10/993,723, filed on Nov. 19, 2004, which claims the benefit of Provisional Patent application Ser. No. 60/552,632, filed on Mar. 12, 2004; Provisional Patent Application Ser. No. 60/541,540, filed on Feb. 3, 2004; Provisional Patent Application Ser. No. 60/523,960, filed on Nov. 21, 2003, and co-pending Non-Provisional patent application Ser. No. 11/366,676, filed on Mar. 3, 2006; each of which is incorporated herein in its entirety.

BACKGROUND OF THE INVENTION

1. Field of the Invention

The present invention relates generally to medical devices and methods configured for the treatment of bone fractures, and more particularly, to a system and method for intramedullary subchondral support fixation (IMSSF) of radial head fractures.

2. Description of the Prior Art

In the medical arts, there is increasing awareness regarding the relevance of radial column integrity across the spectrum of elbow injuries. Cadaveric studies have supported the view that an intact radial head provides secondary support to the elbow joint in valgus stress. When there is compromise to the medial collateral ligament, the main buttress against valgus deviation is provided by the radial head. The in-vitro varus-valgus laxity after ligament disruption is further increased after radial head excision. Restoration of the radial head using radial head arthroplasty, for example, must be carried out in combination with ligament repair to restore normal elbow stability.

The specific lesions in the so-called "unhappy triad" include medial collateral ligament tear, coronoid fracture and radial head fracture. The combination of these injuries renders the elbow joint unstable with the potential for early advanced joint degeneration and deformity. A number of studies have been performed relating to the issue of posterolateral instability in cadaveric specimens with intact collateral ligaments after radial head excision in combination with coronoid lesions. These studies emphasize the key role of the radial column. In the studies, the degree of rotational displacement of the ulna was measured after a valgus-supination moment was applied. Excision of the radial head significantly destabilized the elbow in posterolateral testing. Frank ulnohumeral dislocation takes place with excision of greater than 30% of the coronoid. Only restoration of the radial head can stabilize the elbow, provided the collateral ligaments remain intact. In radial head fracture cases, it is therefore desirable to restore the radial head whenever possible.

A wide variety of devices have been developed for the support and treatment of various bone fractures, and more particularly, the support and treatment of radial head fractures. A common approach which is currently used to treat radial head fractures is open reduction and internal fixation of radial head fractures.

Open reduction and internal fixation of radial head fractures frequently requires the application of a plate in the non-articular (non-cartilagenous) portion of the fractured head. In most instances, proper exposure of the fractured head requires the release and later repair of the key ligamentous structures. One of those important structures requiring release is the annular ligament. It is desirable to avoid dividing this ligament because it is critical to the stability of the proximal end of the radius. In addition, standard plating techniques frequently fail to meet the mechanical requirement for physiological loads which are applied to the radial head throughout the range of motion of the radius. Recent advances in the current art for fixation methods of radial head fractures have included modular fixed angle assembly techniques, in which bone screws are extended through a plate placed on the non-articular portion of the fractured head and into the head. Because these current art plates are applied to the surface of the bone, their use requires release of important ligaments such as the annular ligament and also results in significant hardware irritation of the surrounding soft tissues. This frequently requires re-operation to ameliorate the effects of irritation. In addition, the current art plates continue to interfere with normal rotation of the radial head in its articulation. Moreover, current plate fixation techniques require that the plate be placed directly on top of the bone and soft tissue sleeve, and this compresses the tenuous blood supply to the radius.

In current plate fixation technology, the plate is often a significant source of irritation to the annular ligament, as the plate lies under the repaired annular ligament. Additionally, current art plates are typically not able to be utilized in such a manner as to preserve the tenuous periosteal sleeve.

In this respect, there is a need in the art for a system and method for intramedullary subchondral support fixation (IMSSF) of radial head fractures which addresses the disadvantages present in existing fixation systems and methods.

SUMMARY OF THE INVENTION

The present invention is directed to a system and method for intramedullary subchondral support fixation (IMSSF) of radial head fractures.

An object of the present invention is to provide a system and method for intramedullary subchondral support fixation of radial head fractures that reduces irritation to the annular ligament.

A further object of the present invention is to provide a system and method for intramedullary subchondral support fixation of radial head fractures wherein there is no implicit interference with articular function of the head of the radius, as the hardware is intra-medullary, or inside the radial medullary cavity.

Another object of the present invention is to provide a system and method for intramedullary subchondral support fixation of radial head fractures wherein injury to the soft tissue attachments of the fracture fragments is avoided by permitting at least some blood supply flow into the fractured bone fragments.

An additional object of the present invention is to provide a system and method for intramedullary subchondral support fixation of radial head fractures which may be utilized without releasing the annular ligament.

A further object of the present invention is to provide a system and method for intramedullary subchondral support fixation of radial head fractures that eliminates the need to make distal incisions.

Yet another object of the present invention is to provide a system and method for intramedullary subchondral support fixation of radial head fractures that eliminates the need to use a distal locking guide to affix an implant to a nonarticular side of a fracture.

It is also an object of the present invention to provide a system and method for intramedullary subchondral support fixation of radial head fractures wherein the configuration of the system includes fasteners bearing a specific configuration in a radial direction from the long axis of the radius and in a divergent direction in its proximal end intended for fixation of the articular end of the fracture.

A further object of the present invention is to provide a system and method for intramedullary subchondral support fixation of radial head fractures wherein the system combines subchondral support in an axial divergent direction with intramedullary application.

Yet another object of the present invention is to provide a system and method for intramedullary subchondral support fixation of radial head fractures which focuses on gaining purchase or fixation in subchondral bone.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 5 is a front perspective view of the illustrative embodiment of the insertion plate illustrated in FIG. 1;

FIG. 6 is a sectional view of the head, neck and shaft portions of a radius having a fractured radial head, more particularly illustrating insertion of the insertion plate illustrated in FIG. 5 in the radius in fixation of radial head fractures.

Like reference numerals refer to like parts throughout the several views of the drawings.

DETAILED DESCRIPTION OF THE PREFERRED EMBODIMENTS

Shown throughout the figures, the present invention relates generally to a system and method which is configured for the treatment of bone fractures, and more particularly, to a system and method for intramedullary subchondral support fixation (IMSSF) of radial head fractures.

Existing plate technology used in the open reduction and internal fixation of radial head fractures is attended by a number of drawbacks, among these being that installation of plates on the non-articular or non-cartilagenous portion of the fractured radial head requires release and later repair of key ligamentous structures including the annular ligament; the plates installed on the radial head are a significant source of irritation to the annular ligament since the plate rests under the repaired annular ligament; the plates are not able to be utilized in such a manner as to preserve the tenuous periosteal sleeve; and the plates interfere with normal rotation of the radial head throughout its range-of-motion articulation. In this regard, the system and method of the present invention overcomes the deficiencies of the current techniques by providing an insertion plate that is configured to be inserted inside the radial medullary cavity along a general central axis of the radius, as will be hereinafter further described.

Figure 1:
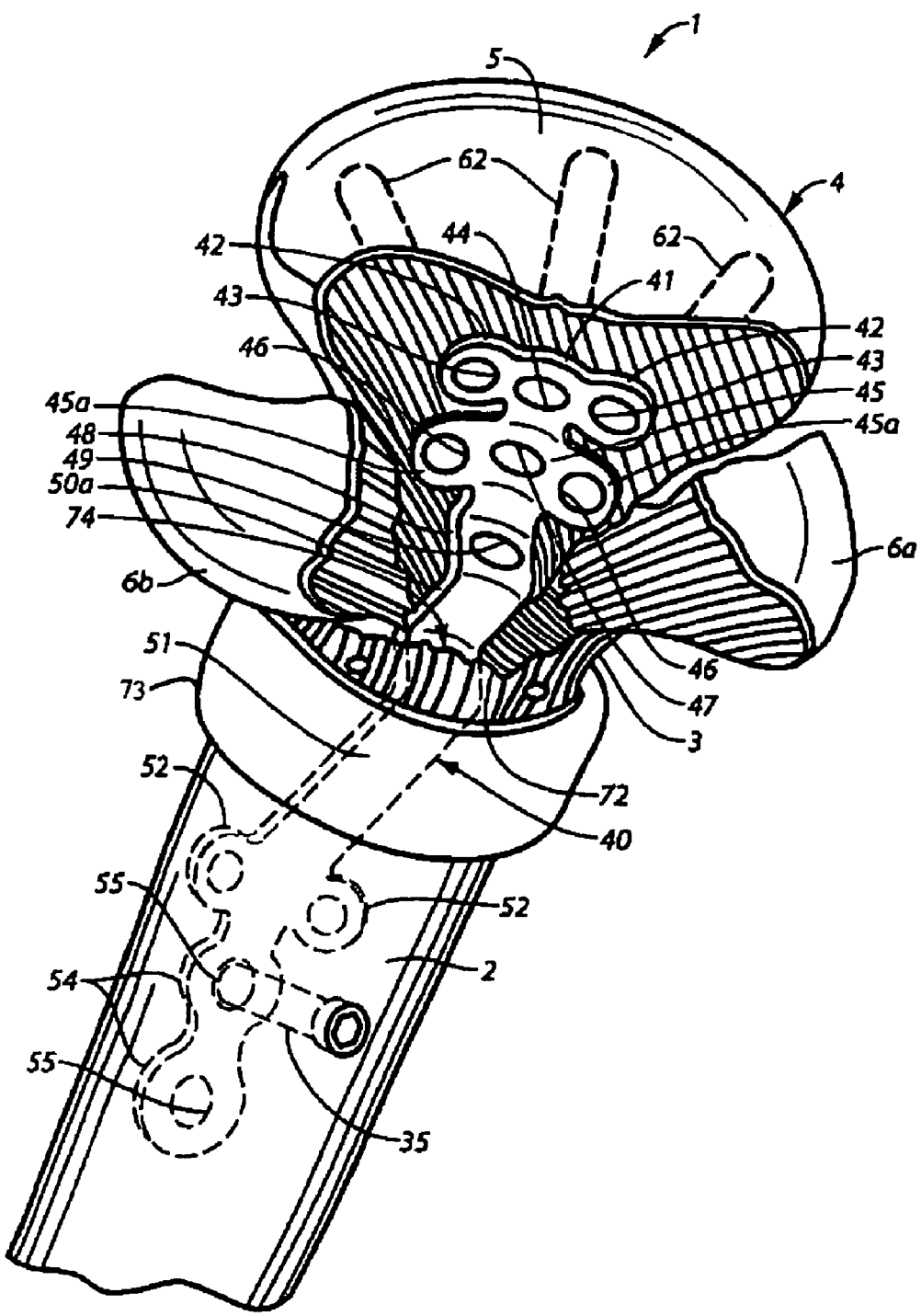
FIG. 1 is a perspective view of a radius (partially in section) having a fractured radial head, more particularly illustrating an insertion plate according to one illustrative embodiment of the present invention inserted in the shaft, neck and fractured radial head portions of the radius in fixation of radial head fractures.

Referring initially to FIG. 1, in the present invention, an insertion plate 40 is introduced as a means of fracture fixation based on sound mechanical principles with the benefit of minimizing soft tissue dissection. This prevents damage to the annular ligament 73 and retains the tenuous blood supply in at least some of the fracture fragments, along what has been termed the "periosteal hinge".

In the remediation of radial head fractures, the safe zone for minimal soft tissue interference is delineated distally by the annular ligament and the soft tissue periosteal layer that provides the tenuous blood supply to some of the fracture fragments. Proximal limits of the safe zone correspond to the non-articular surface of the radial head. In the present invention, the insertion plate is applied intra-focally and one or more fasteners or modular pegs are inserted into the most medial head fragment. The distal plate screws are applied also in an intra-focal fashion to engage one cortex along the intact neck or shaft without the need of a guide as is the case in locking intramedullary nails. Once partial articular stability to the neck-diaphysis is re-established, the fracture becomes a simpler type II lesion. The remaining articular fragments are reduced and fixed with standard technique.

Preparatory to the method of the present invention; the surgeon should have at his or her disposal a modular fixed angle mini-plating system. Any of the following systems can be used for the rigid intramedullary fixation:

SYNTHES® 2.4 modular blade plate or similar. Most plates are found in the Hand Modular System from SYNTHES®. However, any of the blade plate systems which are commercially specific t-plates from Hand Innovations are the most rigid and are well suited for this application.

When none of these is available, the surgeon may fabricate a mini-blade plate from any commercially available plates sized 2.7 to 2.0 mm.

In a number of complicated injuries with significant comminution, it is necessary to have a radial head replacement system available until completion of the case. A back-up plan for head replacement is an excellent bail-out option. In fracture-dislocations with significant ligamentous injuries, radial head replacement of the non-floating type is advisable.

In carrying out the method, the surgery is carried out under tourniquet ischemia and under fluoroscopy. For heavy muscular patients the larger C-arm is preferred for optimal radiographic visualization. For thinner patients, a small C-arm may be adequate. The patient is placed in the supine position and scout fluoroscopy is done before the sterile preparation to insure that anteroposterior, lateral and oblique radiographs can be performed with minimal limb manipulation. Live fluoroscopy is invaluable in this procedure.

Two different approaches of the method are described. For most fractures the approach of Kocher in between the anconeous muscle and the extensor carpi ulnaris is developed. In most injuries there is some damage to the radial collateral and or ulnar lateral collateral ligament at the level of the lateral epicondyle. If there is no significant injury, the surgical approach can result in some elevation of these important structures which should be repaired to the bone at the end of the procedure. Bone anchors or transosseous sutures are indicated. The capsulotomy is carried out along the anterior border of the ulnar lateral collateral ligament. At the anterior aspect of the lateral epicondyle, the radial collateral ligament is elevated sufficiently for visualization. The capsulotomy is extended to the proximal border of the annular ligament. The hematoma is evacuated. Organized clot is removed with the Frazier tip of the suction hose. The fracture is evaluated critically and the fracture fragments identified. Those fracture fragments with some intact periosteal hinge are handled with extreme care to avoid entire devascularization. Most fractures will have an element of impaction of one of the articular fragments. The impacted fragment is elevated intra-focally with a freer elevator. Once the medial articular fragment is properly reduced with respect to the neck-shaft, the plate is applied intra-focally. The lateral fragments are held sufficiently retracted in the manner of an open book to allow the insertion of the plate and the fixation. The first point of fixation is to the medial articular fragment. The threaded drill guide is assembled to the plate and a properly sized drill bit is used. The drill hole should not violate the articular surface into the lesser sigmoid notch. Alternatively, when a modular system is not available, a mini-plate is bent as a small blade plate. The first drill hole is done transversely into the medial articular fragment to accommodate the horizontal component of the blade.

At this time the proper neck length is re-established. The drill is aimed in an anterograde lateral to medial direction from the fracture site intra-focally, through one of the plate holes and into the intact medial-distal cortex of the distal neck-diaphysis. After confirming that the preliminary reduction is appropriate, a second screw may be applied to enhance the fixation of the plate distally, again engaging only one cortex. A second or third peg or screw can be applied to the proximal end of the plate and into the medial articular fragment. At this point the fracture has been converted into a simpler type II fracture with partial articular-neck-diaphysis continuity. The lateral articular fracture fragments are then reduced in the manner of closing the book. These articular fragments are fixed with standard lagging counter-sink technique. At times one can be fortunate and apply one of these lag screws into one of the plate holes. It is quickly evident that it is difficult to engage the plate at this time because it lies buried in the center of the proximal radius. Fluoroscopy is useful during the procedure. In the end the construct has minimal or no prominence. Articular congruence and stability through the range of forearm and elbow motion is the goal. Axial loads across the articular surface are transmitted axially along the plate and to the intact diaphysis. It is possible and advisable to fill the intramedullary voids with bone graft to enhance the stability and healing. Bone substitutes are not recommended for this application. Delayed union at the fracture site may cause failure of fracture fixation at the plate-bone interphase failure after repetitive range of motion during rehabilitation.

The capsule and the oblique ligamentous interval between the radial collateral ligament and the ulnar lateral collateral ligament is closed with 2-0 or 3-0 non-absorbable ETHIBOND® sutures.

For supracondylar fractures undergoing olecranon osteotomy, or for central fracture dislocations with severe comminution of the proximal ulna, the radial head can be approached from its distal articular surface. The fracture fragments are held slightly separated while the plate is inserted intra-focally along the neck and shaft of the proximal radius. In this situation the fixation can be done to any of the articular fracture fragments. The distal locking is done, as before, intra-focally and into the intact cortex of the neck-diaphysis. The rest of the operation is virtually the same.

Figure 2:
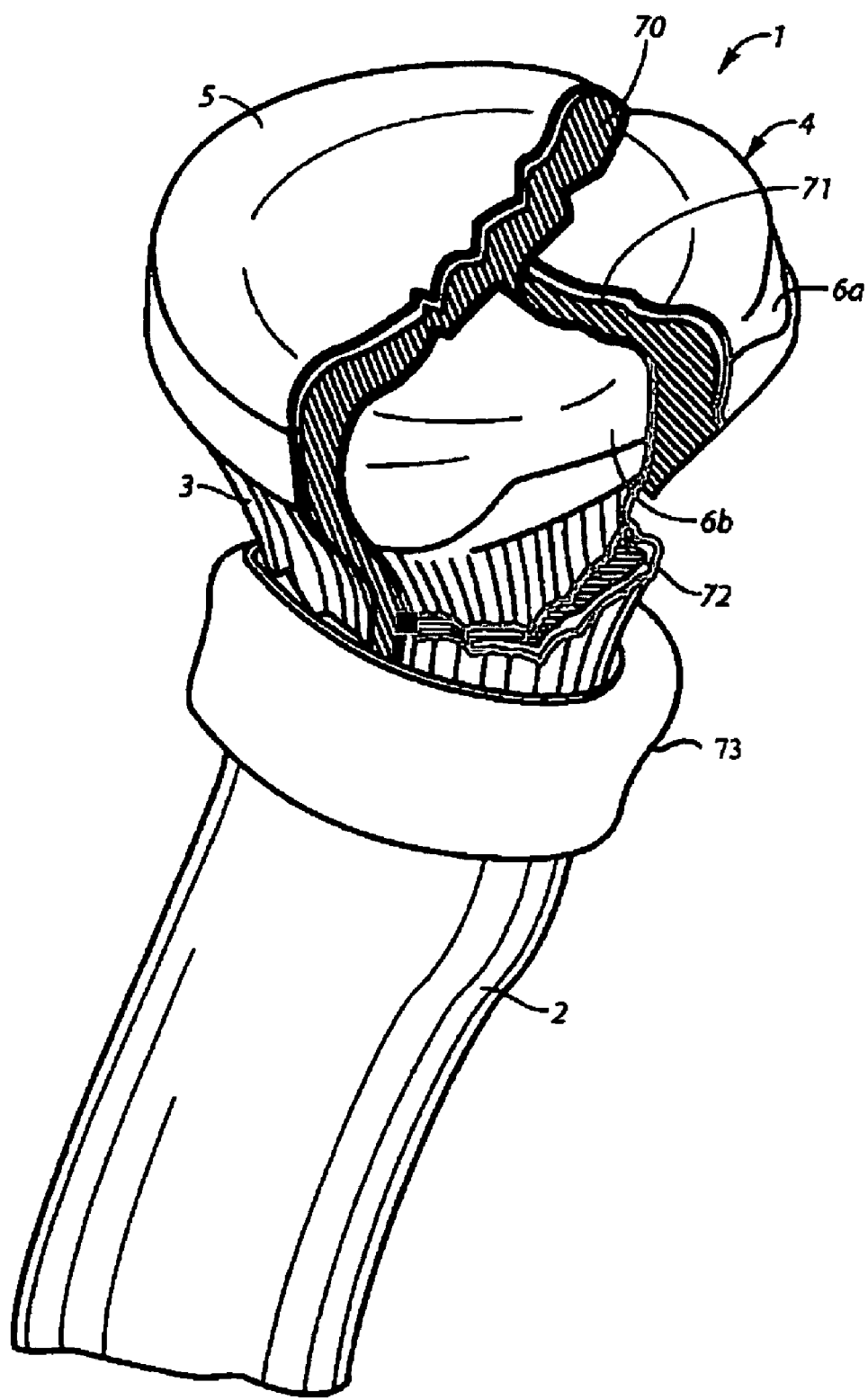
FIG. 2 is a perspective view of a radius (partially in section) having a typical fractured radial head.

Referring to FIG. 2, an example of a radius 1 having a fractured radial head 4 which is suitable for fixation according to the present invention is illustrated. The radius 1 includes an elongated radial shaft 2 (shown partially in section), a radial neck 3 extending from the radial shaft 2 and a radial head 4 extending from the radial neck 3. The radial head 4 is the proximal head of the radius 1. For purposes of illustration and description herein, the radial head 4 includes a first articular radial head fragment 5 and a second articular radial head fragment 6. A medullary cavity 7 (FIG. 6) extends through the radial shaft 2 and contains bone marrow (not illustrated). For purposes of illustration and description herein, in the fractured radial head 4, the second articular radial head fragment 6 is further divided into third and fourth articular radial head fragments 6a, 6b which are separated from the first articular radial head fragment 5 along a fracture line 70. The third and fourth articular radial head fragments 6a, 6b are separated from each other along a fracture line 71 and from the radial neck 3 along a fracture line 72.

Referring next to FIG. 5, an insertion plate 40 according to one illustrative embodiment of the system is shown. The insertion plate 40 is typically stainless steel and includes a head segment 41 from which extends a pair of oppositely-disposed head flanges 42. The head flanges 42 may be disposed at a generally obtuse angle with respect to each other. A flange fastener opening 43 extends through each head flange 42. A middle fastener opening 44 may extend through the head segment 41.

A neck segment 45 extends at a generally 90-degree angle from the head segment 41 along a neck bend 56. A pair of oppositely-disposed neck flanges 45a extends from the neck segment 45. The neck flanges 45a may be disposed at a generally obtuse angle with respect to each other. Flange fastener openings 46 extend through the respective neck flanges 45a. A middle fastener opening 47 may extend through the neck segment 45.

A shaft segment 48 extends at a generally obtuse angle from the neck segment 45 at a shaft bend 57. A shaft fastener opening 49 extends through the shaft segment 48. A pair of shaft connecting segments 50 extends from the shaft segment 48 at a shaft bend 58. The first shaft connecting segment 50a, which extends from the shaft bend 58, is disposed at a generally 90-degree angle with respect to the shaft segment 48. The shaft connecting segments 50 are connected to each other along a middle bend 59, with the second shaft connecting segment 50b disposed at a generally 90-degree angle with respect to the first shaft connecting segment 50a. A fastener opening 67 extends through the second shaft connecting segment 50b.

A shaft segment 51 extends from the second shaft connecting segment 50b along a shaft bend 60. A pair of connected tail segments 54 extends from the shaft segment 51 at a generally obtuse angle along a tail bend 61. Tail fastener openings 55 extend through the respective tail segments 54. A pair of shaft flanges 52, each having a flange fastener opening 53, extends from the junction between the tail segments 54 and the shaft segment 51. The shaft flanges 52 may be disposed at a generally obtuse angle with respect to each other.

Referring next to FIGS. 1 and 5-7 of the drawings, an illustrative embodiment of the intramedullary subchondral support fixation (IMSSF) of radial head fractures method according to the present invention is carried out as a surgical procedure, typically as follows. As illustrated in FIG. 1, the fractured radial head 4 is initially divided by separating or peeling the third and fourth articular radial head fragments 6a, 6b of the second articular radial head fragment 6 from the first articular radial head fragment 5 along the fracture line 70 (FIG. 2) and folding the third and fourth articular radial head fragments 6a, 6b along the fracture line 72. The third and fourth articular radial head fragments 6a, 6b are separated from each other along the fracture line 71. IMMSF can be accomplished with minimal manipulation of the fracture fragments 6a, 6b and preservation of the tenuous periosteal sleeve in these fragments. It is desirable to avoid injury to the soft tissue attachments of the fracture fragments because some blood supply may flow into the fractured fragments, favoring healing and minimizing resorption. At the base of the third and fourth articular radial head fragments 6a, 6b, an incision 74 is made from the fracture line 72, through and generally along the longitudinal axis of the radial shaft 2 of the radius 1. As illustrated in FIG. 6, the incision 74 extends into the medullary cavity 7 of the radial shaft 2.

After the incision 74 is made, the insertion plate 40 is inserted in the fractured radius 1. Accordingly, as illustrated in FIG. 1, the head segment 41, neck segment 45 and shaft segment 48 extend along the fractured surface of the first articular radial head fragment 5. The shaft connecting segments 50a, 50b; the shaft segment 51; and the tail segments 54 are inserted in the incision 74.

Head fastener channels (not illustrated) are drilled through the flange fastener openings 43 of the head flanges 42 and the middle fastener opening 44 of the head segment 41, respectively, and into the first articular radial head fragment 5. Head fasteners 62 (one of which is illustrated) are inserted through the flange fastener openings 43 and middle fastener opening 44, respectively, and threaded into the respective registering head fastener channels. Therefore, the head fasteners 62 fasten the head segment 41 and head flanges 42 of the insertion plate 40 to the first articular radial head fragment 5.

Figure 7:
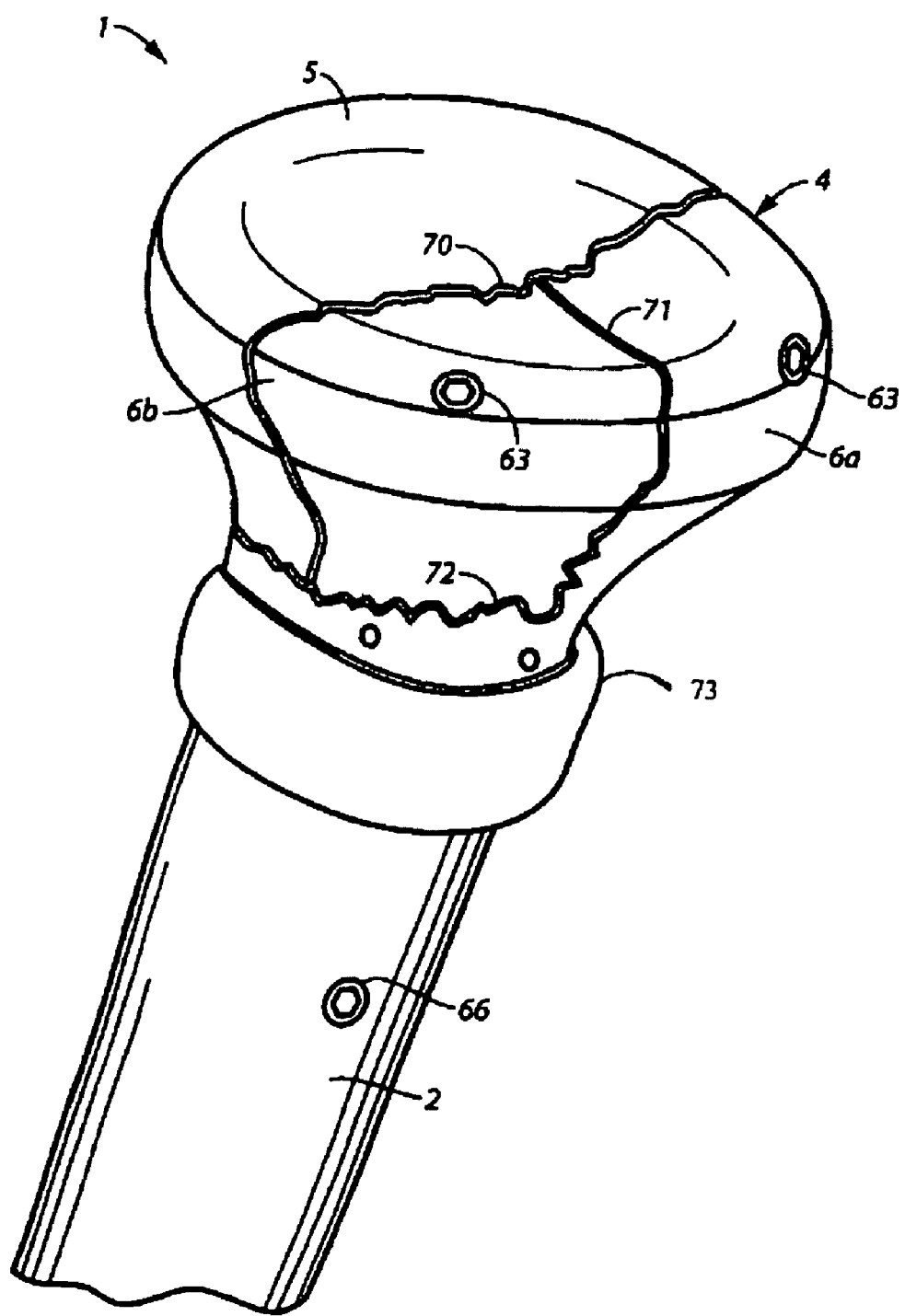
FIG. 7 is a perspective view of a fractured radial head in a fixed configuration after insertion of the insertion plate in the radius as illustrated in FIGS. 1 and 6.

Neck fastener channels (not shown) are drilled through the respective third and fourth articular radial head fragments 6a, 6b and the flange fastener openings 46 in the respective neck flanges 45a of the insertion plate 40 and into the first articular radial head fragment 5. As illustrated in FIGS. 6 and 7, neck fasteners 63 (one of which is illustrated In FIG. 6) are extended through the respective fastener channels in the third and fourth articular radial head fragments 6a, 6b and registering flange fastener openings 46 of the insertion plate 40 and threaded into the registering neck fastener channels in the first articular radial head fragment 5. Shaft fastener channels (not illustrated) are drilled through the shaft fastener opening 49 of the shaft segment 48 and through the shaft fastener opening 67 of the second shaft connecting segment 50b, respectively, and into the radial shaft 2. As illustrated in FIG. 6, shaft fasteners 64 and 65 are extended through the respective shaft fastener openings 49 and 67 and threaded into the respective registering shaft fastener channels. The shaft fastener 64 typically extends through the fracture line 72.

A tail fastener channel (not illustrated) is additionally drilled through the radial shaft 2 and the tail fastener opening 55 of one of the tail segments 54. A tail fastener 66 is threaded through the tail fastener channel and extended through the tail fastener opening 55. Accordingly, the head fasteners 62 secure the insertion plate 40 to the first articular radial head fragment 5; the neck fasteners 63 secure the respective third and fourth articular radial head fragments 6a, 6b to the insertion plate 40 and first articular radial head fragment 5; the shaft fastener 64 extends through the fracture line 72 and secures the radial head 4 to the radial shaft 2; and the shaft fastener 65 and tail fastener 66 secure the insertion plate 40 to the radial shaft 2.

Figure 3:
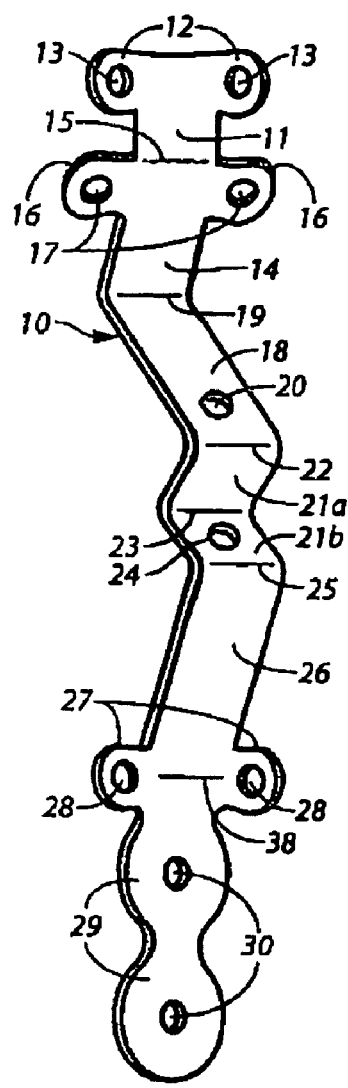
FIG. 3 is a front perspective view of an insertion plate according to an alternative illustrative embodiment of the present invention.

Referring next to FIG. 3, an insertion plate 10 according to another illustrative embodiment of the system is shown. The insertion plate 10 is typically stainless steel and includes a head segment 11 from which extends a pair of oppositely-disposed head flanges 12. The head flanges 12 may be disposed at a generally obtuse angle with respect to each other. A flange fastener opening 13 extends through each head flange 12.

A neck segment 14 extends at a generally obtuse angle from the head segment 11 along a neck bend 15. A pair of oppositely-disposed neck flanges 16 extends from the neck segment 14. The neck flanges 16 may be disposed at a generally obtuse angle with respect to each other. Flange fastener openings 17 extend through the respective neck flanges 16.

A shaft segment 18 extends at a generally 90-degree angle from the neck segment 14 along a shaft bend 19. A shaft fastener opening 20 extends through the shaft segment 18. A pair of shaft connecting segments 21 extends from the shaft segment 18 at a shaft bend 22. The first shaft connecting segment 21a extends from the shaft bend 22 and is disposed at a generally 90-degree angle with respect to the shaft segment 18. The shaft connecting segments 21 are connected to each other along a middle bend 23, with the second shaft connecting segment 21b disposed at a generally 90-degree angle with respect to the first shaft connecting segment 21a. A fastener opening 24 extends through the second shaft connecting segment 21b.

A shaft segment 26 extends from the second shaft connecting segment 21b along a shaft bend 25. The shaft segment 26 is disposed at a generally 90-degree angle with respect to the second shaft connecting segment 21b. A pair of connected tail segments 29 extends from the shaft segment 26 at a generally obtuse angle along a tail bend 38. The tail segments 29 are disposed at a generally obtuse angle with respect to the shaft segment 26. Tail fastener openings 30 extend through the respective tail segments 29. A pair of shaft flanges 27, each having a flange fastener opening 28, extends from the junction between the tail segments 29 and the shaft segment 26. The shaft flanges 27 may be disposed at a generally obtuse angle with respect to each other.

Figure 4:
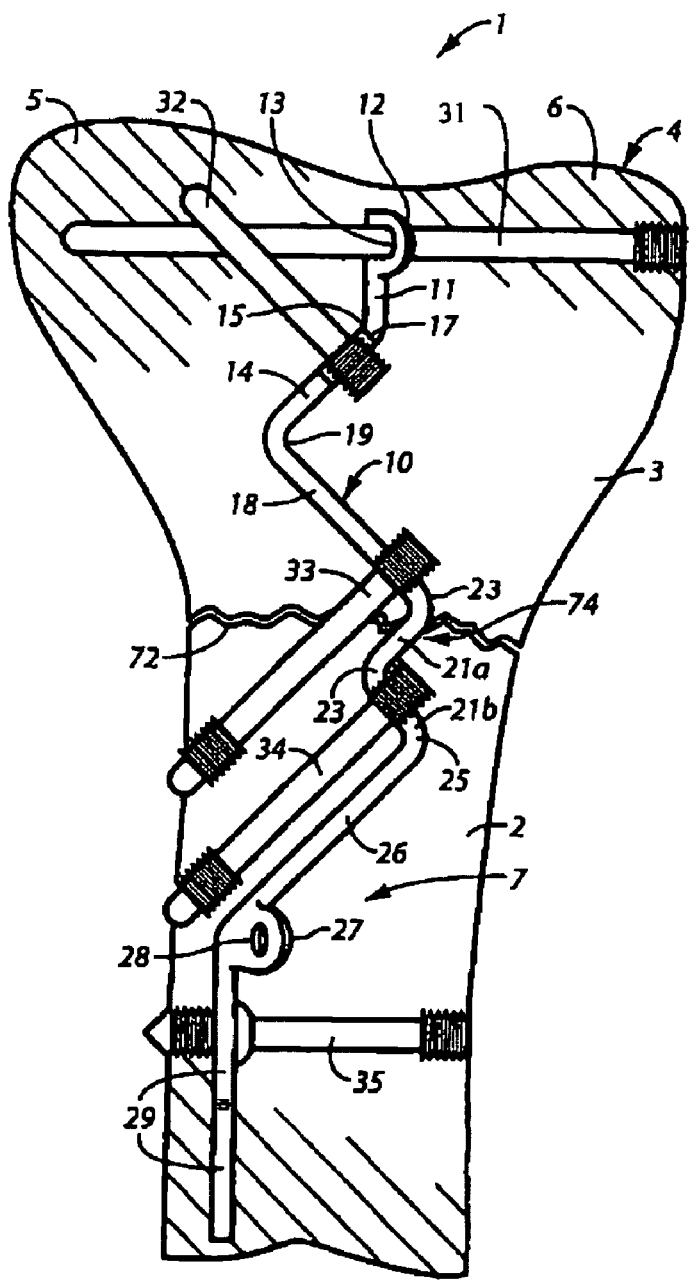
FIG. 4 is a sectional view of the head, neck and shaft portions of a radius having a fractured radial head, more particularly illustrating insertion of the insertion plate illustrated in FIG. 3 in the radius in fixation of radial head fractures.

Referring again to FIG. 1 and to FIG. 4 of the drawings, in another illustrative embodiment of the method, the intramedullary subchondral support fixation of radial head fractures is carried out as a surgical procedure, typically in a similar manner as was heretofore described with respect to FIGS. 1, 6 and 7. Accordingly, the fractured radial head 4 is initially divided by separating or peeling the third and fourth articular radial head fragments 6a, 6b of the second articular radial head fragment 6 from the first articular radial head fragment 5 along the fracture line 70 (FIG. 7) and folding the third and fourth articular radial head fragments 6a, 6b along the fracture line 72. The third and fourth articular radial head fragments 6a, 6b are separated from each other along the fracture line 71. At the base of the third and fourth articular radial head fragments 6a, 6b, an incision 74 is made from the fracture line 72, through and generally along the longitudinal axis of the radial shaft 2 of the radius 1. As illustrated in FIG. 4, the incision 74 extends into the medullary cavity 7 of the radial shaft 2.

After the incision 74 is made, the insertion plate 10 is inserted in the fractured radius 1. Accordingly, the head segment 11, neck segment 14 and shaft segment 18 extend along or adjacent to the fractured surface of the first articular radial head fragment 5. The shaft connecting segments 21a, 21b; the shaft segment 26; and the tail segments 29 are inserted in the incision 74.

Neck fastener channels (not illustrated) are drilled through the respective flange fastener openings 17 of the neck flanges 16 and into the first articular radial head fragment 5. Neck fasteners 32 (one of which is illustrated in FIG. 4) are inserted through the respective flange fastener openings 17 and threaded into the neck fastener channels extending into the first articular radial head fragment 5. Accordingly, the neck fasteners 32 secure the insertion plate 10 to the first articular radial head fragment 5.

Head fastener channels (not illustrated) are drilled through the respective third and fourth articular radial head fragments 6a, 6b and respective flange fastener openings 13 of the head flanges 12 and into the first articular radial head fragment 5. Head fasteners 31 (one of which is illustrated in FIG. 4) are inserted through the flange fastener openings 13 and threaded into the respective registering fastener channels. Therefore, the head fasteners 31 fasten the third and fourth articular radial head fragments 6a, 6b to the insertion plate 10 and the first articular radial head fragment 5.

A shaft fastener channel (not illustrated) is drilled through the shaft fastener opening 20 of the shaft segment 18 and into the radial shaft 2. As illustrated in FIG. 4, a shaft fastener 33 (one of which is illustrated in FIG. 4) is extended through the shaft fastener opening 20 and threaded into the registering shaft fastener channel. The shaft fastener 33 typically extends through the fracture line 72. A second shaft fastener channel (not illustrated) is additionally drilled through the radial shaft 2 and the fastener opening 24 of the shaft connecting segment 21b. A shaft fastener 34 is extended through the fastener opening 24 threaded into the second fastener channel. Accordingly, the shaft fastener 33 extends through the fracture line 72 and secures the radial head 4 to the radial shaft 2. The shaft fastener 34 secures the insertion plate 10 to the radial shaft 2. A tail fastener channel (not illustrated) is drilled through the radial shaft 2 and through a tail fastener opening 30 in one of the tail segments 29. A tail fastener 35 is threaded into the tail fastener channel and extends through the tail fastener opening 30. The tail fastener 35 additionally secures the insertion plate 10 to the radial shaft 2.

After completion of the IMSSF method, the same complications which are reported in standard ORIF should be anticipated. Failure of fixation in theory can be dealt with radial head excision and hardware removal. Infection at the fracture site is rare in radial head replacement. Deep infection postoperatively can be managed with hardware removal. In most instances of infection, the radial head may be excised and the hardware removed. Temporary implantation of antibiotic bone cement, together with repeated debridement procedures and appropriate intravenous antibiotics, are usually sufficient in eliminating the infection.

Persistent instability resulting from failure of fixation may be addressed by radial head excision and replacement arthroplasty with ligament repair whenever necessary.

Rehabilitation following the IMSSF method is carried out typically by immobilizing the elbow in neutral forearm rotation with the elbow in 90 deg of flexion, or in slight extension if the elbow is sufficiently stable. A well-padded double sugar tongue splint or a posterior long arm splint is well-suited for immediate post-operative immobilization. The patient is strongly encouraged to keep the limb elevated. Passive and active assisted range-of-motion is begun at seven to ten days after surgery. A removable posterior splint in 70 deg of flexion is fabricated by the therapist. The patient is encouraged to remove the splint several times per day and carry out several sets of the range-of-motion exercises at the elbow and the forearm. At six to eight weeks postoperative, passive progressive splints such as a DYNASPLINT® may be used to regain elbow extension and forearm supination. Flexion and pronation are more easily recovered.

It will be appreciated by those skilled in the art that the IMSSF method of the present invention offers several advantages over current plate fixation techniques for the repair of radial head fractures. The IMSSF method can be carried out in such a manner as to preserve the tenuous periosteal sleeve and other soft tissue attachments of the fracture fragments such that the blood supply to the fragments is preserved. This favors healing and minimizes resorption. Current art plate fixation techniques require that the plate be placed directly on the bone and soft tissue sleeve, thereby compressing the blood supply. Furthermore, IMSSF can be accomplished without releasing the annular ligament. There are implicit advantages in avoiding damage to this important structure even if it is repaired at the end of a procedure. Moreover, the plates attached to the bone using current techniques are a continuous source of irritation to the annular ligament since the plate rests beneath the annular ligament. Rotation of the radius about the ulna results in abrasion of the ligament as it contacts the underyling plate.

Another advantage associated with IMSSF is the lack of implicit interference with articular function of the radial head since the hardware is intra-medullary, or inside the bone medullary cavity. Furthermore, the IMSSF system and method does not require distal incisions or the use of a distal locking guide to affix a plate to the non-articular side of the fracture. Fasteners used to affix the insertion plate to the non-articular side of the fracture can be placed through the fracture site in a manner of fixation which can be termed "distal intra-focal fixation", or DIFF.

Another advantage of the IMSSF system and method is that the configuration of the insertion plate and the fasteners bears a specific configuration in a radial direction from its long axis and in a divergent direction in its proximal end intended for fixation of the articular end of the fracture. It has been found that the specific configuration provides unprecedented fixation, not only in its ability to engage and support the soft bone but also in its ability to transfer loads across the articular end of the head. The configuration of the insertion plate and its fasteners are also aimed to gain purchase or fixation in part of the bone known as the subchondral bone, which has better mechanical quality than soft metaphyseal bone.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for intramedullary subchondral support fixation of a radial head having radial head fragments and a radial shaft extending from said radial head, comprising:

providing an insertion plate having a head segment, a neck segment disposed at a generally 90-degree angle to said head segment, a first shaft segment disposed at a generally obtuse angle to said neck segment, a first shaft connecting segment disposed at a generally 90-degree angle to said first shaft segment, a second shaft connecting segment disposed at a generally 90-degree angle to said first shaft segment, a second shaft segment disposed at a generally 90-degree angle to said second shaft connecting segment, and at lest one tail segment disposed at a generally obtuse angle to said second shaft segment;

inserting said insertion plate in said radial shaft of said radius;

attaching a first one of said head segment and said neck segment of said insertion plate to said radial head;

attaching said radial head fragments to a second one of head segment and said neck segment of said insertion plate;

attaching said first shaft segment and said second shaft connecting segment to said radial shaft; and attaching said tail segment to said radial shaft.

2. The method of claim 1 further comprising a pair of head flanges extending from said head segment and a pair of flange fastener openings extending through said pair of head flanges, respectively.

3. The method of claim 2 further comprising of a pair of neck flanges extending from said neck segment, a pair of shaft flanges extending from one of said first shaft segment and said second shaft segment and a plurality of flange fastener openings extending through said pair of neck flanges and said pair of shaft flanges, respectively.

* * * * *